United States Patent
Ikefuji

(10) Patent No.: US 11,060,054 B2
(45) Date of Patent: Jul. 13, 2021

(54) SPECIMEN CONTAINER

(71) Applicant: SCREEN HOLDINGS CO., LTD., Kyoto (JP)

(72) Inventor: Kunio Ikefuji, Kyoto (JP)

(73) Assignee: SCREEN HOLDINGS CO., LTD., Kyoto (JP)

( * ) Notice: Subject to any disclaimer, the term of this patent is extended or adjusted under 35 U.S.C. 154(b) by 305 days.

(21) Appl. No.: 16/024,667

(22) Filed: Jun. 29, 2018

(65) Prior Publication Data

US 2019/0010438 A1     Jan. 10, 2019

(30) Foreign Application Priority Data

Jul. 5, 2017  (JP) .............................. JP2017-131651
Sep. 25, 2017 (JP) .............................. JP2017-183180
Apr. 27, 2018 (JP) .............................. JP2018-086223

(51) Int. Cl.
  *C12M 1/32*  (2006.01)
  *C12M 1/34*  (2006.01)
  *C12M 1/00*  (2006.01)

(52) U.S. Cl.
  CPC ............ *C12M 23/12* (2013.01); *C12M 23/00* (2013.01); *C12M 41/44* (2013.01)

(58) Field of Classification Search
  CPC ...... C12M 23/12; C12M 23/00; C12M 23/16; C12M 41/44; C12M 29/10; C12M 41/48;
  (Continued)

(56) References Cited

U.S. PATENT DOCUMENTS 7,785,098 B1 *  8/2010  Appleby ............... B29C 33/302
                                            264/319
8,058,060 B2 *  11/2011  Esser ..................... C12M 25/04
                                            435/305.2
(Continued)

FOREIGN PATENT DOCUMENTS

EP   3 434 370 A1      1/2019
GB   2539935 A    *   1/2017   ............ C12M 25/14
(Continued)

OTHER PUBLICATIONS

Machine Translated Description of JP2012249547 A (Year: 2012).*
(Continued)

*Primary Examiner* — Michael L Hobbs
*Assistant Examiner* — Lenora A Abel
(74) *Attorney, Agent, or Firm* — McDermott Will & Emery LLP

(57) ABSTRACT

A specimen container includes a well having an opening to store fluid. An opening plane, and first and second cross sections have outer peripheral shapes dissimilar to each other and in a plan view, the second cross section is contained in the first cross section and the first cross section is contained in the opening plane. The opening plane, and the first and second cross sections are defined in a horizontal posture of the body. The opening plane is a projected plane of the opening of the well on a horizontal plane. The first cross section is a horizontal cross section of the internal space taken at a position corresponding to a first depth defined vertically downwardly from the opening. The second cross section is a horizontal cross section of the internal space taken at a position corresponding to a second depth greater than the first depth.

16 Claims, 13 Drawing Sheets

(58) Field of Classification Search
CPC .... B01J 2219/00596; B01J 2219/00659; B01J 2219/00722; B01J 19/0046; B01L 7/52; B01L 7/00; B01L 7/54; B01L 2300/0654; B01L 2300/0819; B01L 2300/1822; B01L 2300/1827; B01L 3/50273; B01L 3/502715; B01L 3/502761; B01L 3/5025; B01L 3/5027; B01L 2400/0457; B01L 2400/0487; B01L 2300/0861; B01L 2300/0848; B01L 2300/0829; G01N 21/6428; G01N 21/6454; G01N 2021/0325; G01N 2021/062; G01N 35/00029; G01N 35/0099; G01N 2035/00148; C12Q 1/686; C12Q 1/6844; C12Q 1/689; C12Q 1/6853; C12Q 1/6848
USPC .......................................... 435/294.1, 305.2
See application file for complete search history.

(56) References Cited

U.S. PATENT DOCUMENTS

| | | | |
|---|---|---|---|
| 9,180,456 B2* | 11/2015 | Malinoski | ............... C08L 67/02 |
| 2010/0028935 A1 | 2/2010 | Ciaiolo et al. | |
| 2010/0221768 A1 | 9/2010 | Akai et al. | |
| 2014/0162351 A1 | 6/2014 | Yamamoto et al. | |
| 2015/0072405 A1* | 3/2015 | Ito | ........................ C12M 23/12 435/288.4 |
| 2015/0313704 A1 | 11/2015 | Thavandiran et al. | |
| 2017/0267960 A1 | 9/2017 | Tsukada et al. | |

FOREIGN PATENT DOCUMENTS

| | | | | | |
|---|---|---|---|---|---|
| GB | 2539935 | A | | 1/2017 | |
| JP | 2010-110262 | A | | 5/2010 | |
| JP | 2012249547 | A | * | 12/2012 | ............ C12M 23/20 |
| JP | 2016-063779 | A | | 4/2016 | |
| KR | 10-2016-0117631 | A | | 10/2016 | |
| WO | 2013/030940 | A1 | | 3/2013 | |
| WO | 2017/183875 | A1 | | 10/2017 | |

OTHER PUBLICATIONS

Extended European Search Report issued in corresponding European Patent Application No. 18179214.4, dated Nov. 2, 2018.
European Office Action issued in corresponding European Patent Application No. 18179214.4-1111, dated Nov. 5, 2019.
Korean Notification of Reason for Refusal issued in corresponding Korean Patent Application No. 10-2018-0070835, dated Jul. 30, 2019, with English Translation.

* cited by examiner

SPECIMEN CONTAINER

CROSS REFERENCE TO RELATED APPLICATION

The disclosure of Japanese Patent Applications enumerated below including specifications, drawings and claims is incorporated herein by reference in its entirety:
No. 2017-131651 filed on Jul. 5, 2017;
No. 2017-183180 filed on Sep. 25, 2017; and
No. 2018-086223 filed on Apr. 27, 2018.

BACKGROUND OF THE INVENTION

1. Field of the Invention

The present invention relates to a specimen container for holding a specimen containing a fluid, particularly to a specimen container used preferably for culturing cells and others in a fluid.

2. Description of the Related Art

In technical fields such as medical and biochemical fields, cells, microorganisms, or tissues (hereinafter called "cells or the like") are cultured in a fluid poured into a container for the purpose of conducting various experiments such as microscopic observation of cells, for example. As an example, a specimen container known by a name such as a microplate, a well plate, or a microtiter plate has multiple recesses called wells arranged in a matrix each having an opening at the upper surface of a plate-like base material and being capable of holding a fluid in internal space of the recess.

The well formed in such a container generally has a configuration formed by combining a cylindrical side wall having a horizontal cross section of a relatively simple shape such as a circle or a rectangle and a flat bottom surface. In one example, the well has a cross-sectional shape changed in the depth direction of the well for a particular purpose. According to a technique described in patent literature 1 (JP2016-063779A), for example, multiple upwardly-pointing protrusions are formed at the bottom surface of a well. The well has a side wall formed as a curved surface having a horizontal cross-sectional area reducing with a shorter distance to the bottom surface of the well. This configuration is intended to grow a cell efficiently and three-dimensionally on the protrusion and to facilitate observation of the growth. According to a technique stated in patent literature 2 (WO2013/030940), a well has a bottom surface provided with a protrusion for culture of a cell and a protrusion indicating a symbol, for example, for making each well discriminable during observation.

The specimen containers of the foregoing conventional techniques are devised mainly for making observation conveniently. Meanwhile, culturing cells or the like in a fluid poured into a specimen container requires action to be taken in response to a problem differing from those described above. For example, cells are cultured in a culture fluid under culture environment maintained at a constant temperature and a constant humidity. In such culture environment, the culture fluid is highly likely to evaporate further. Hence, a technique to determine whether the amount of the culture fluid in a well being used for culture is appropriate or not has been desired. In a specimen container such as a well plate having a large number of wells arranged in a matrix, observing a fluid surface in each well from the side is particularly difficult. Thus, a device allowing a fluid amount to be visually checked from above in a simple way has been desired. However, such a technique has not been suggested so far.

If a fluid amount in a well is insufficient, a culture fluid is added, if necessary. Further, to remove a metabolite resulting from activation of a substance such as a cell, the culture fluid may be exchanged regularly. In such cases, as the amount or the state of the culture fluid changes between wells, an operator is required to determine the state of the culture fluid in each well individually and add or exchange the culture fluid, if necessary. The culture fluid is poured into a well using a tool such as a pipette with a thin tip, for example. However, determining the position of the tip of such a tool promptly and correctly by hand relative to a well is not an easy work. Hence, this work has a disadvantage in terms of workability such as being time-consuming. Additionally, it is also likely that a substance such as a cell being cultured will be damaged by being touched by the tip of the tool.

SUMMARY OF THE INVENTION

The present invention has been made based on the foregoing problem. A first object of the present invention is to provide a technique implemented in a specimen container used for culture of cells or the like and allowing a determination of the amount of a fluid stored in the container in a simple way through visual check. Further, a second object of the preset invention is to provide means for facilitating work of pouring the fluid into the specimen container.

One aspect of the present invention is intended for a specimen container including a body to which a well having an opening at an upper end and capable of storing a fluid in internal space is disposed. To achieve the first object, an opening plane, a first cross section and a second cross section have outer peripheral shapes dissimilar to each other; and in a plan view, the second cross section is contained in the first cross section and the first cross section is contained in the opening plane. Here, the opening plane, the first cross section and the second cross section are defined in a horizontal posture of the body as follows. The opening plane is a projected plane of the opening of the well on a horizontal plane. The first cross section is a horizontal cross section of the internal space taken at a position corresponding to a predetermined first depth defined vertically downwardly from the opening. Further, the second cross section is a horizontal cross section of the internal space taken at a position corresponding to a second depth greater than the first depth.

More specifically, the specimen container may include a rising part extending from a side wall of the well toward a center area in the internal space. In one configuration, the rising part includes a portion appearing in the first cross section and absent in the second cross section, and a portion appearing both in the first cross section and the second cross section. In another configuration, a part of the side wall of the well forms a rising part extending in an external direction from the internal space. The rising part includes a portion appearing in the first cross section and absent in the second cross section, and a portion appearing both in the first cross section and the second cross section.

Another aspect of the present invention is intended for a specimen container including a body to which a well having an opening at an upper end and capable of storing a fluid in internal space is disposed. To achieve the first object, in the specimen container, a rising part extending upwardly from a bottom of the well along a side wall of the well is disposed and the rising part includes a portion appearing in a first cross section and absent in a second cross section and a portion appearing both in the first cross section and the second cross section. Here, the first cross section and the second cross section are defined in a horizontal posture of the body as follows. The first cross section is a horizontal cross section of the internal space taken at a position corresponding to a predetermined first depth defined vertically downwardly from the opening. The second cross section is a horizontal cross section of the internal space taken at a position corresponding to a second depth greater than the first depth.

Visual observation of the well of the specimen container held in a horizontal posture from above with a fluid poured into the well shows that the shape of a fluid surface indicates the cross-sectional shape of the internal space of the well at a fluid surface height at the time of the observation. According to the invention having the foregoing configuration, a cross-sectional shape changes in response to a depth viewed through the opening of the well. This means that the shape of the fluid surface observed from above changes in response to a fluid surface height at the time of the observation. Specifically, the foregoing configuration makes it possible to determine the amount of the fluid stored in the internal space in a simple way based on the shape of the fluid surface determined through viewing of the well from above.

According to the present invention, the rising part provided partially at the side wall of the well functions as a positional reference for an operator to insert the tip of a tool such as a pipette for pouring the fluid into the well. Specifically, by making the tip of the tool for pouring the fluid into the well abut on the rising part, the position of the tool relative to the well is determined easily. This can largely enhance the workability of the operation by the operator and working accuracy. This also prevents damage of a cell or the like with the tip of the tool. In this way, the second object is achieved.

As described above, according to the present invention, the cross-sectional shape of the well changes in response to a depth from the opening of the well, and the shape of the fluid surface viewed from above changes in response to the amount of the fluid stored in the internal space of the well. This makes it possible to determine the amount of the fluid in a simple way through visual observation of the shape of the fluid surface. Further, the position of the tip of the tool for operation on the liquid can be determined easily and correctly relative to the well, thereby enhancing workability of such operation and working accuracy.

The above and further objects and novel features of the invention will more fully appear from the following detailed description when the same is read in connection with the accompanying drawing. It is to be expressly understood, however, that the drawing is for purpose of illustration only and is not intended as a definition of the limits of the invention.

DETAILED DESCRIPTION OF THE PREFERRED EMBODIMENTS

Figure 1A:
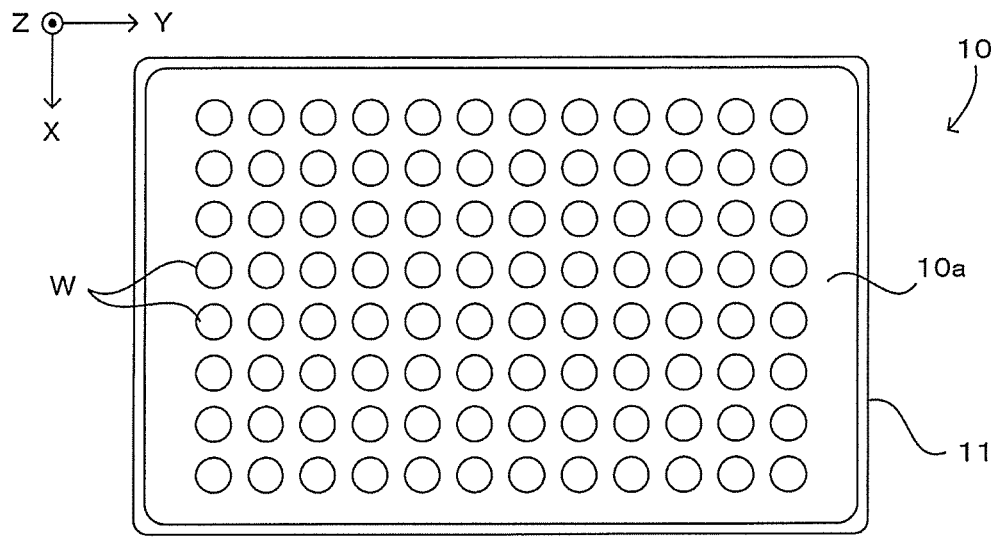
FIGS. 1A and 1B are drawings showing an entire configuration of a well plate as an example of a specimen container according to the present invention.
Figure 1B:
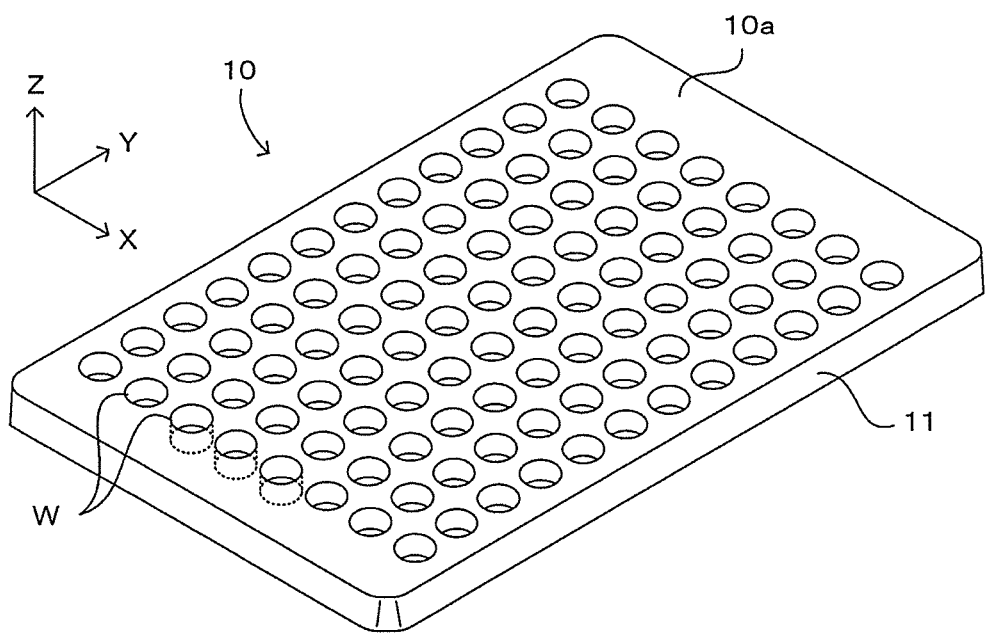

FIGS. 1A and 1B are drawings showing an entire configuration of a well plate as an example of a specimen container according to the present invention. More specifically, FIG. 1A is a top view of a well plate 10 and FIG. 1B is a perspective view of the well plate 10. The well plate 10 has a configuration including a plate-like base material 11 made of plastic, for example, and multiple wells W arranged regularly in a two-dimensional matrix with a constant pitch at the base material 11. Each well W has a substantially circular cylindrical shape with an open upper surface and a closed bottom surface (alternatively, a tapered truncated conical shape having a horizontal cross-sectional area reducing gradually with a shorter distance to a bottom surface). In this example, wells W are provided at 12×8 (=96) positions. However, the number of wells provided at one plate is determined freely.

While the well plate 10 is in such a posture as to place an upper surface 10a of the well plate 10 horizontally, the well plate 10 is capable of holding a fluid in internal space of each well W surrounded by a side wall surface and a bottom surface. In medical and biochemical fields, the well plate 10 is applicable preferably for the purpose of culturing cells or the like in a culture fluid poured into the wells W and preparing a specimen, for example. FIGS. 1A and 1B show a state where the well plate 10 is held in a horizontal posture. In FIGS. 1A and 1B, an XY plane shows a horizontal plane and a +Z direction shows a vertically upward direction.

The bottom surface of each well W may be formed integrally with the base material 11. Alternatively, well bottom surfaces may be formed by blocking the bottoms of through holes provided at the base material 11 to extend in the Z direction (vertical direction) with a resin sheet, for example. If a specimen prepared by culture is to be used for the purpose such as microscopic observation or photomicroscopy, the well bottom surfaces are preferably made of a material transparent to illumination light applied during observation.

The internal configuration of the well W will be described next. Internal space of each well in an ordinary well plate having been commercialized is defined as space surrounded by a side wall having a horizontal cross section of a relatively simple shape such as a circle or a rectangle and a substantially flat bottom surface. Thus, it is difficult to determine the height of a fluid surface when a well is observed from above. In particular, in a well plate having a large number of wells arranged in two dimensions, even observing a fluid surface in each well from the side is impossible. This makes it difficult to estimate the amount of a fluid held in each well W through visual check.

If the well plate 10 with a culture fluid poured into the wells W is placed inside an incubator at a constant temperature and a constant humidity for the purpose of culturing cells or the like, for example, the culture fluid evaporates further with time. In this case, it is likely that the concentration of a component in the culture fluid will become too high to cause inappropriate culture environment. If a cultured specimen is used for optical observation, drop of a fluid surface makes the lens effect noticeable resulting from a meniscus occurring at the fluid surface. This may cause a trouble in the observation.

To prevent such a problem before it happens, the amount of a fluid held in each well W should be evaluated as needed and the fluid should be added, if necessary. As described above, however, it is difficult to determine a fluid surface height in each well through visual check in an ordinary well plate. This has made it impossible to evaluate a fluid amount in a simple way. The following describes examples of the internal configuration of a well W allowing a fluid amount in the well W to be determined in a simple way through visual check from above.

Figure 2:
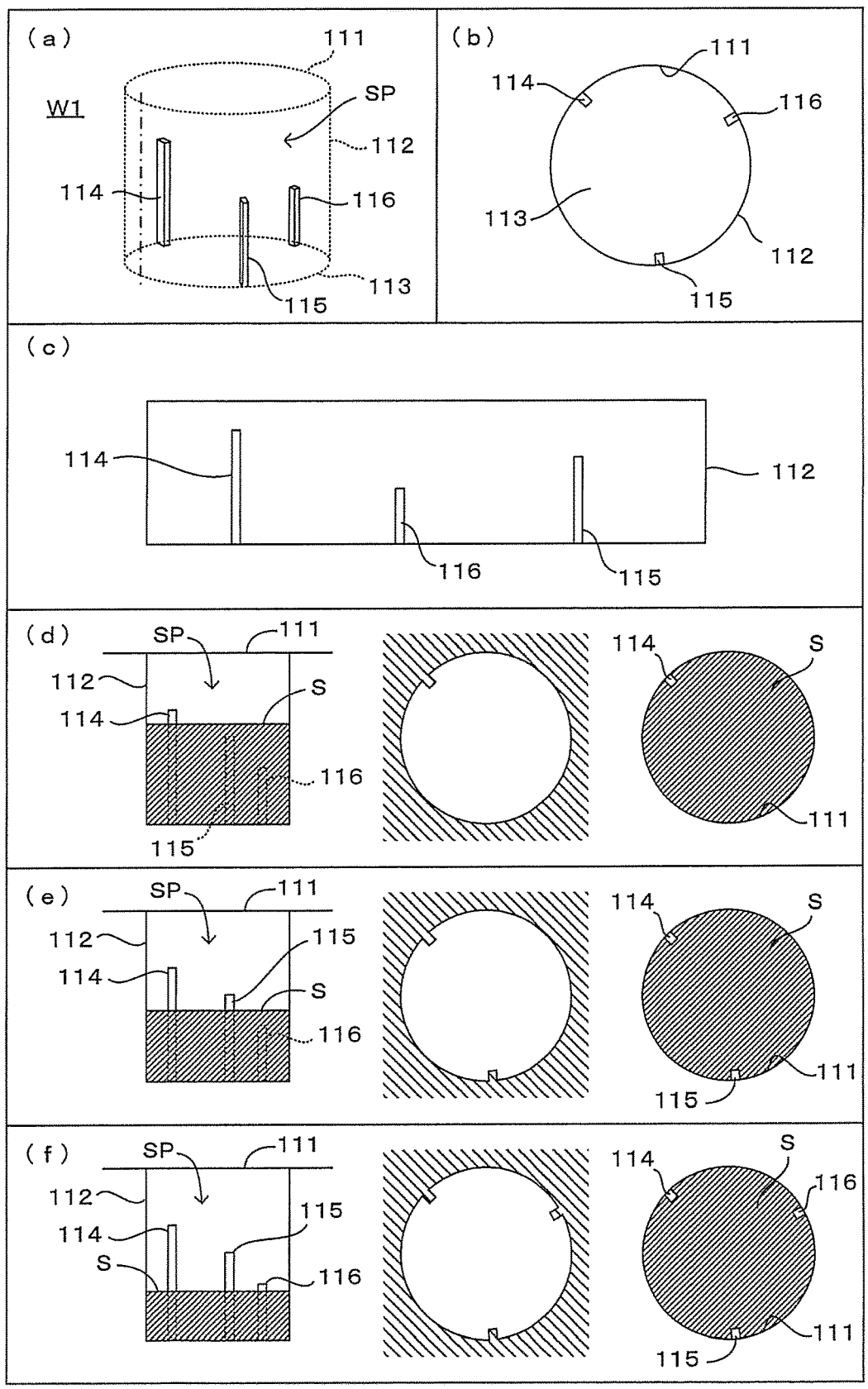
FIG. 2 is a drawing showing a first example of a well having an internal configuration according to the present invention.

FIG. 2 is a drawing showing a first example of a well having an internal configuration according to the present invention. In FIG. 2, a field (a) is a transparent view schematically showing the internal configuration of the well. To show the internal configuration clearly, edge lines corresponding to edges of an opening, a side wall, and a bottom surface of the well are indicated by dotted lines. A field (b) shows the well viewed from above in the absence of a fluid in the well. A field (c) is an exploded view prepared by cutting the well side wall along alternate long and short dash lines indicated in the field (a).

A field (d), a field (e), and a field (f) show how the well is viewed in different ways resulting from different fluid amounts. In each of these fields, a left view shows the well viewed from the side, a center view is a horizontal cross-sectional view of the well cut at a fluid surface, and a right view shows the shape of the fluid surface when the well is viewed from above. The field (d) shows a case where a fluid amount is relatively large. The field (e) shows a case where a fluid amount is smaller than the fluid amount in the case shown in the field (d). The field (f) shows a case where a fluid amount is still smaller than the fluid amount in the case shown in the field (e).

The foregoing description of each of the fields (a) to (f) will be applied as it is to each of FIGS. 3 to 9 referred to later.

A well W1 according to the first example shown in FIG. 2 has an opening plane 111 at the top and is capable of storing a fluid in internal space SP of the well W1 surrounded by a substantially circular cylindrical side wall 112 and a substantially flat bottom surface 113. The well W1 includes three rising portions 114, 115, and 116 extending upwardly from the bottom surface 113 in columnar shapes and are arranged along the side wall 112. The rising portions 114, 115, and 116 contact the side wall 112, so that each of the rising portions 114, 115, and 116 is a structure extending like a rib from the side wall 112 toward a central area in the well internal space SP. While each of the rising portions 114, 115, and 116 is described as having a rectangular horizontal cross-sectional shape, the shape of the horizontal cross section may be determined freely.

As shown in the field (b), when the well W is viewed from above, the respective top surfaces of the rising portions 114, 115, and 116 and the bottom surface 113 appear inside the opening plane 111. As shown in the fields (a) and (c), regarding a height in the vertical direction with respect to the bottom surface 113, the rising portion 114 is the highest, the rising portion 115 is the second highest, and the rising portion 116 is the lowest. Thus, in a depth direction corresponding to a downwardly vertical direction from the opening plane 111, the top surface of the rising portion 114 is at the shallowest position, that of the rising portion 115 is at the next shallowest position, and that of the rising portion 116 is at the deepest position.

It is assumed that a fluid of a relatively large amount is poured into the well W1 having the foregoing configuration, the top of the rising portion 114 is exposed upwardly from a fluid surface S, and the tops of the rising portions 115 and 116 are below the fluid surface S as shown in the field (d). Actually, a meniscus occurs at a fluid surface. Meanwhile, the fluid surface S in the left view of each of the fields (d) to (f) shows a height at a section contacting the well side wall 112 and is illustrated as a horizontal line accordingly. The center view in the field (d) is a cross-sectional view of the well W taken at a horizontal cross section corresponding to a fluid surface height at this stage. As shown in this view, the cross section at this stage has a shape with a cutout corresponding to the rising portion 114 formed at a part of a substantially circular outer periphery defined by the side wall 112.

As shown in the right view in the field (d), viewing the fluid surface S from above through the opening plane 111 shows that only the rising portion 114 is exposed from the substantially circular fluid surface S and the other rising portions 115 and 116 are hidden under the fluid. In other words, if the fluid surface S viewed from above is in the state shown in the right view in the field (d), the fluid at this stage can be said to have such a relatively large amount as to expose only the rising portion 114.

Meanwhile, if the fluid has such an amount as to expose the top of the rising portion 115 from the fluid surface S in addition to the rising portion 114 as shown in the field (e), the cross-sectional shape of the well W taken at a horizontal cross section at a fluid surface height at this stage differs from the shape shown in the field (d). More specifically, as shown in the center view in the field (e), a cutout corresponding to the rising portion 115 is added to the cross section shown in the center in the field (d). As shown in the right view in the field (e), viewing the fluid surface S from above at this stage shows that the rising portions 114 and 115 are exposed from the fluid surface S.

When a fluid amount is reduced further to expose the tops of all the three rising portions 114, 115, and 116 from the fluid surface S as shown in the left view in the field (f), the cross-sectional shape of the well W1 taken at a fluid surface height at this stage is additionally given a cutout accordingly corresponding to the rising portion 116. Viewing the fluid surface S from above at this stage also shows that all the three rising portions 114, 115, and 116 are exposed from the fluid surface S.

As described above, by the provision of the rising portions 114, 115, and 116 at the side wall 112 of the well W1 having different heights from the bottom surface 113 of the well W1 (specifically, having different depths from the opening plane 111), the cross-sectional shape of the well internal space SP taken at a fluid surface height changes in response to a fluid amount. This also changes a way in which the fluid surface S is viewed from above. This is usable in evaluating a fluid amount in the well W1 through observation of the fluid surface S from above.

For example, the following can be understood by setting the height of the rising portion 114 at a fluid surface height corresponding to an upper limit of the amount of a fluid to be held in the well W1 and setting the height of the rising portion 116 at a fluid surface height corresponding to a lower limit of the amount of the fluid to be held in the well W1. If none of the rising portions is exposed when a fluid surface is observed from above, the amount of the fluid is excessive. By contrast, if all the rising portions are exposed, the amount of the fluid is too small. If at least one rising portion is exposed and at least one rising portion is hidden under the fluid, this state shows that a fluid amount in the well W1 is within an appropriate range.

However, only providing two rising portions corresponding to an upper limit and a lower limit of a fluid amount is not sufficient for learning the position of a fluid amount in the appropriate range. Hence, reduction in a fluid amount cannot be detected until the rising portion 116 becomes exposed from a fluid surface, failing to achieve the purpose of learning timing of adding a fluid.

In this regard, the rising portion 115 having a height intermediate between the height of the rising portion 114 and that of the rising portion 116 is provided. This makes it possible to determine whether a fluid amount is approximate to the upper limit or to the lower limit. Specifically, if only the rising portion 114 is exposed when a fluid surface is viewed from above, a fluid of such an amount as to place the fluid surface at a height exceeding the height of the rising portion 115 is ensured. Meanwhile, if the rising portions 114 and 115 are exposed, this state shows that a fluid amount approximates further to the lower limit. If the top of the rising portion 115 is placed at a position corresponding to a fluid surface height of a fluid amount as a rough indication for addition, the need for addition of the fluid can be determined on condition that exposure of the rising portion 115 is confirmed. Conversely, unless the rising portion 115 is exposed, the addition can be determined to be unnecessary.

As described above, the well W1 according to the first example includes the three rising portions 114, 115, and 116 arranged along the side wall 112 and having different depths from the opening plane 111. This makes it possible to learn change in the height of the fluid surface S resulting from change in a fluid amount through observation of the fluid surface S from above. Rising portions provided at at least two places are functional as indications of an upper limit and a lower limit of a fluid amount. The number of rising portions may be increased in response to the need for determining a fluid amount based on more scales. A fluid amount is indicated by the number of rising portions exposed from a fluid surface, making it possible to determine a fluid amount without requiring specialized knowledge.

In some conventional well plates, a well has a side wall of what is called a tapered shape by which the horizontal cross section of well internal space becomes smaller with a shorter distance to the bottom surface of the well. In the well of this configuration, the shape of a fluid surface viewed from above does not change but the area of the fluid surface changes in response to the height of the fluid surface. This may be usable as information for determining a fluid amount. However, the mere change in size is hard to determine through visual observation. In some cases, a comparison from a certain standard may be required. Like in the foregoing example, changing the outer peripheral shape of the horizontal cross section of internal space into dissimilar shapes in response to a depth allows even a user without deep knowledge to evaluate a fluid amount easily. The rising portions are arranged along the side wall 112, so that they do not influence culture and observation of a substance such as a cell at a central area in the well seriously.

To allow change in the cross-sectional shape of well internal space resulting from change in a fluid surface height to be detected through observation from above, a structure to hide a fluid surface defining the cross-sectional shape and prohibit visual recognition from above is required to be absent above the fluid surface. Such absence may be achieved by determining the shape of each part in such a manner that one cross section taken at any depth position in the well internal space SP (a cross section at a depth zero, specifically, a cross section including the opening plane 111) covers any cross section at a deeper position completely in a plan view.

In the example of FIG. 2, each of the rising portions 114, 115, and 116 has a columnar shape of a constant cross-sectional shape extending upwardly from the bottom surface 113. In this way, the foregoing requirement is satisfied. As long as the foregoing requirement is satisfied, change in the shape of each part is permissible. For example, the side wall 112 may have a tapered shape by which a horizontal cross section becomes smaller with a shorter distance to the bottom surface 113. As another example, each of the rising portions 114, 115, and 116 may have a cross-sectional area larger at a lower position than at an upper position.

Different examples of wells having internal configurations according to the present invention will be described below sequentially. The foregoing example and each of the examples descried below differ in the shape of a rising portion and resultant change in a shape appearing at a fluid surface. Meanwhile, the basic principle of trying to indicate a fluid amount based on change in the shape of the fluid surface is common between the examples. Thus, a configuration or a function in each of the following examples common to that of the foregoing example will not be described in detail and differences from the foregoing example will mainly be described.

Figure 3:
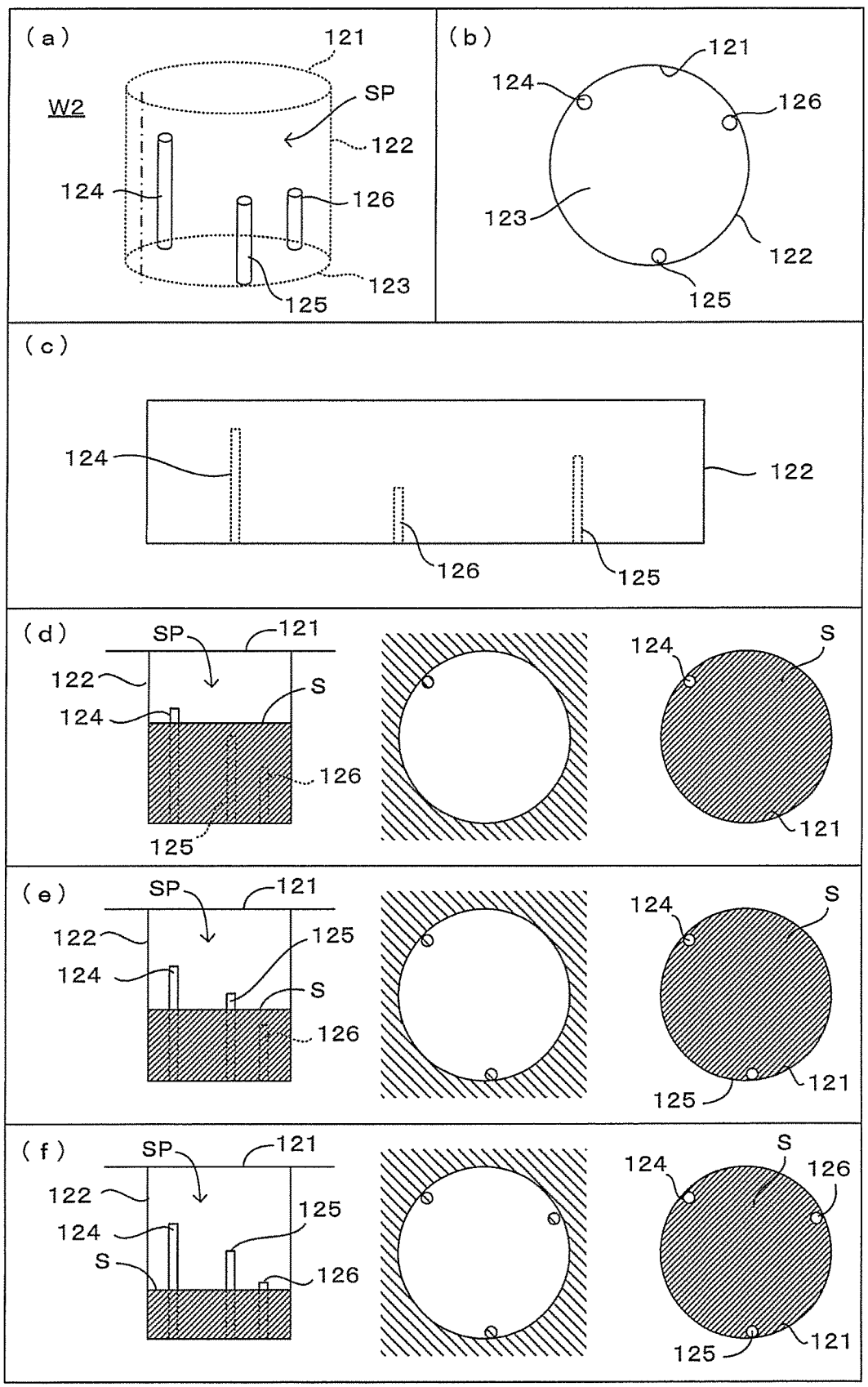
FIG. 3 is a drawing showing a second example of a well having an internal configuration according to the present invention.

FIG. 3 is a drawing showing a second example of a well having an internal configuration according to the present invention. Each field in FIG. 3 shows the same view as in the corresponding field in FIG. 2. A well W2 according to the second example shown in FIG. 3 includes rising portions 124, 125, and 126 having circular columnar shapes extending upwardly from a bottom surface 123 of the well W2 and are arranged along a side wall 122 of the well W2, instead of the rising portions 114, 115, and 116 of the well W1 according to the first example extending inwardly from the side wall 112 into rib-like shapes. The cross-sectional shape of the rising portion is not limited to a circular but may be determined freely. Each of the rising portions 124, 125, and 126 may contact the side wall 122 of the well W2 or may be separated from the side wall 122.

As shown in the field (b), when the well W2 having this configuration is viewed from above, the top surfaces of the rising portions 124, 125, and 126 are contained in a circular region corresponding to an opening plane 121. As shown in the fields (d) to (0, if each of the rising portions 124, 125, and 126 is separated from the side wall 122 of the well W2, change in the height of the fluid surface S in the well internal space SP does not change the outer peripheral shape (in this case, a circular shape) of the cross section of the internal space SP taken at the position of a fluid surface height. The number of circular shapes corresponding to the respective cross sections of the rising portions and contained in the outer peripheral shape changes in response to a fluid surface height.

More specifically, in a state shown in the field (d) where the fluid surface S is at a relatively high position, the cross section of the rising portion 124 having a top at a higher position than the fluid surface S is contained in the circle showing the outer peripheral shape. In a state shown in the field (e) where the fluid surface S is at a lower position, the cross sections of the rising portions 124 and 125 having their tops at higher positions than the fluid surface S are contained in the circle showing the outer peripheral shape. In a state shown in the field (f) where the fluid surface S is at the lowest position, the tops of all the rising portions are at higher positions than the fluid surface S. Thus, the cross sections of all the rising portions 124, 125, and 126 are contained in the circle showing the outer peripheral shape.

As shown in the right views in the fields (d) to (f), together with such changes in the cross-sectional shape, the number of rising portions exposed from the fluid surface S changes in response to the height of the fluid surface S when the fluid surface S is observed from above through the opening plane 121. Thus, like in the case of the well W1 according to the first example, an upper limit and a lower limit of a fluid amount, information for learning timing of requiring addition, etc. can be acquired through visual check of the fluid surface S by properly setting the height of the top of each of the rising portions 124, 125, and 126. According to the conventional technique described above, the protrusion is formed at a central area of a bottom surface and configured to contribute to culture of a cell positively. By contrast, according to this example, the rising portion 124 and the other rising portions are provided only at positions near the well side wall 122. Thus, the shape of the bottom surface can be determined freely. For example, a substantially flat shape causes no influence on culture and observation of a cell or the like. The rising portion according to the present invention and a protrusion such as that disclosed by the foregoing conventional technique may be used in combination.

Figure 4:
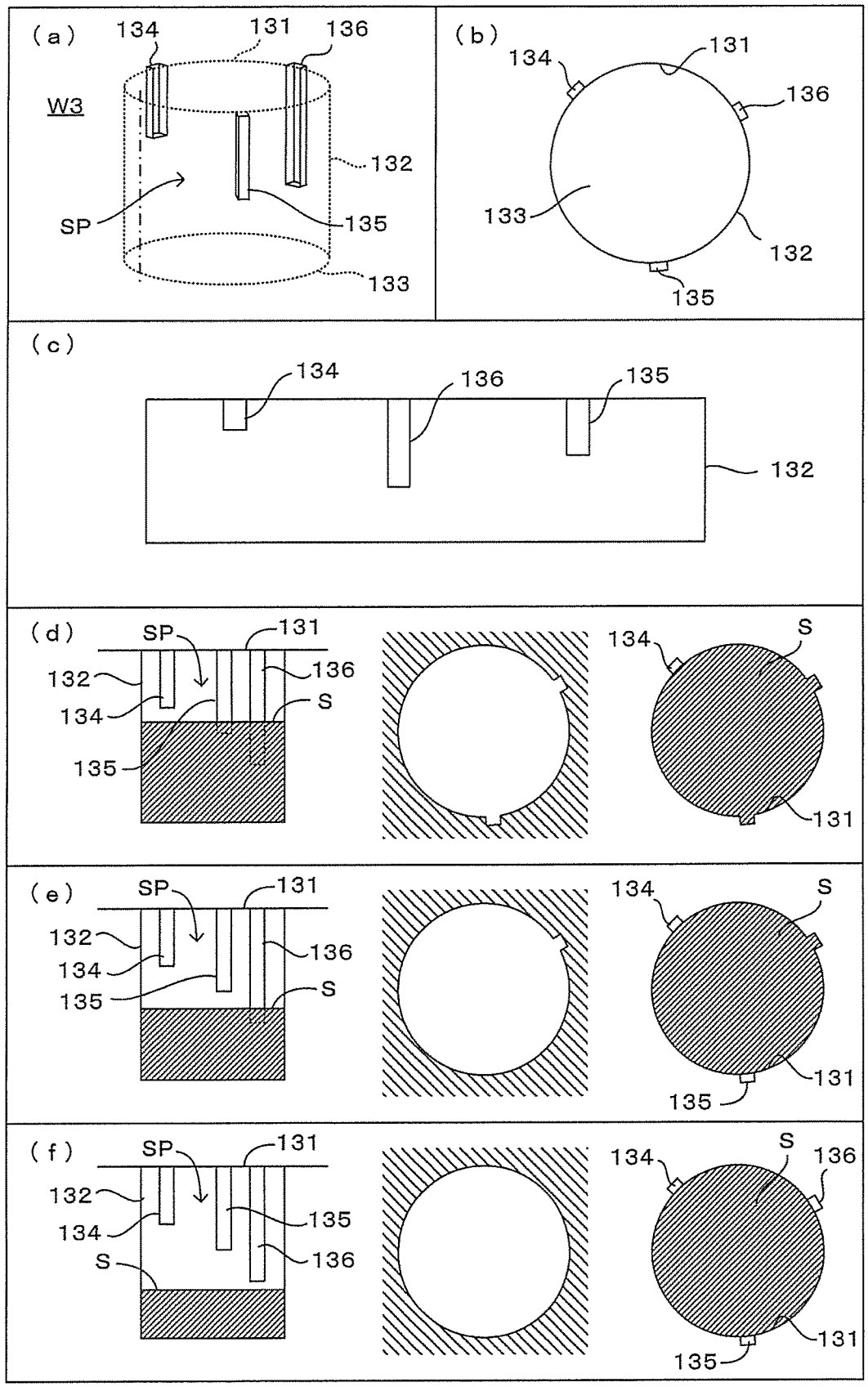
FIG. 4 is a drawing showing a third example of a well having an internal configuration according to the present invention.

FIG. 4 is a drawing showing a third example of a well having an internal configuration according to the present invention. As shown in the field (a), a well W3 according to the third example includes rising portions 134, 135, and 136 extending outwardly from a side wall 132, instead of the rising portions 114, 115, and 116 of the well W1 according to the first example extending from the side wall 112 toward a central area in the well internal space SP. When viewed from external space, the rising portions 134, 135, and 136 can also be called recesses like grooves having surfaces retreating from the side wall 132. The horizontal cross-sectional shape of each of these rising portions may be determined freely.

Based on the foregoing request for the cross section of the well internal space SP taken at one horizontal cross section to cover all cross sections taken at deeper positions, each of the rising portions 134, 135, and 136 according to this example extends downwardly from an opening plane 131 formed at the top of a well plate. The rising portions 134, 135, and 136 have bottoms at different heights (specifically, have different depths from the opening plane 131). Meanwhile, the positions of all the bottoms of the rising portions 134, 135, and 136 are shallower than the position of a well bottom surface 133. These bottoms function in the same way as the respective tops of the rising portions 114, 115, and 116 of the well W1 according to the first example.

As shown in the field (b), in the absence of a fluid in the well W3, the well bottom surface 133 and the bottom of each of the rising portions 134, 135, and 136 is recognized when the well W3 is observed from above through the opening plane 131. Meanwhile, if a fluid has such an amount as to place the bottoms of the rising portions 135 and 136 below the fluid surface S and place the bottom of the rising portion 134 above the fluid surface S as shown in the field (d), the cross section of the well internal space SP taken at a fluid surface height at this stage has a shape including a circle corresponding to the side wall 132 and externally extending portions on the circle corresponding to the positions of the rising portions 135 and 136. Thus, when the fluid surface S is observed from above through the opening plane 131, the bottoms of the rising portions 135 and 136 are hidden under the fluid and only the bottom of the rising portion 134 is exposed.

As shown in the fields (e) and (f), together with change in the height of the fluid surface S, the outer peripheral shape of the cross section of the well W3 changes to further change the shape of the fluid surface S observed from above. Specifically, with reduction in a fluid amount, the bottom of the rising portion 135 and the bottom of the rising portion 136 become exposed sequentially from the fluid surface S. Therefore, like in the case of the first example, information about the height of the fluid surface S, specifically, about a fluid amount can be acquired based on a situation of exposure of each rising portion observed from above.

As described above, in the configuration where the rising portion is provided to extend outwardly from the side wall, as a fluid surface drops, the number of rising portions appearing at a cross section taken at a corresponding fluid surface height is reduced further. Meanwhile, the bottom of a portion having disappeared from the cross section becomes exposed from the fluid surface S, so that this bottom is easily recognizable through observation from above.

Figure 5:
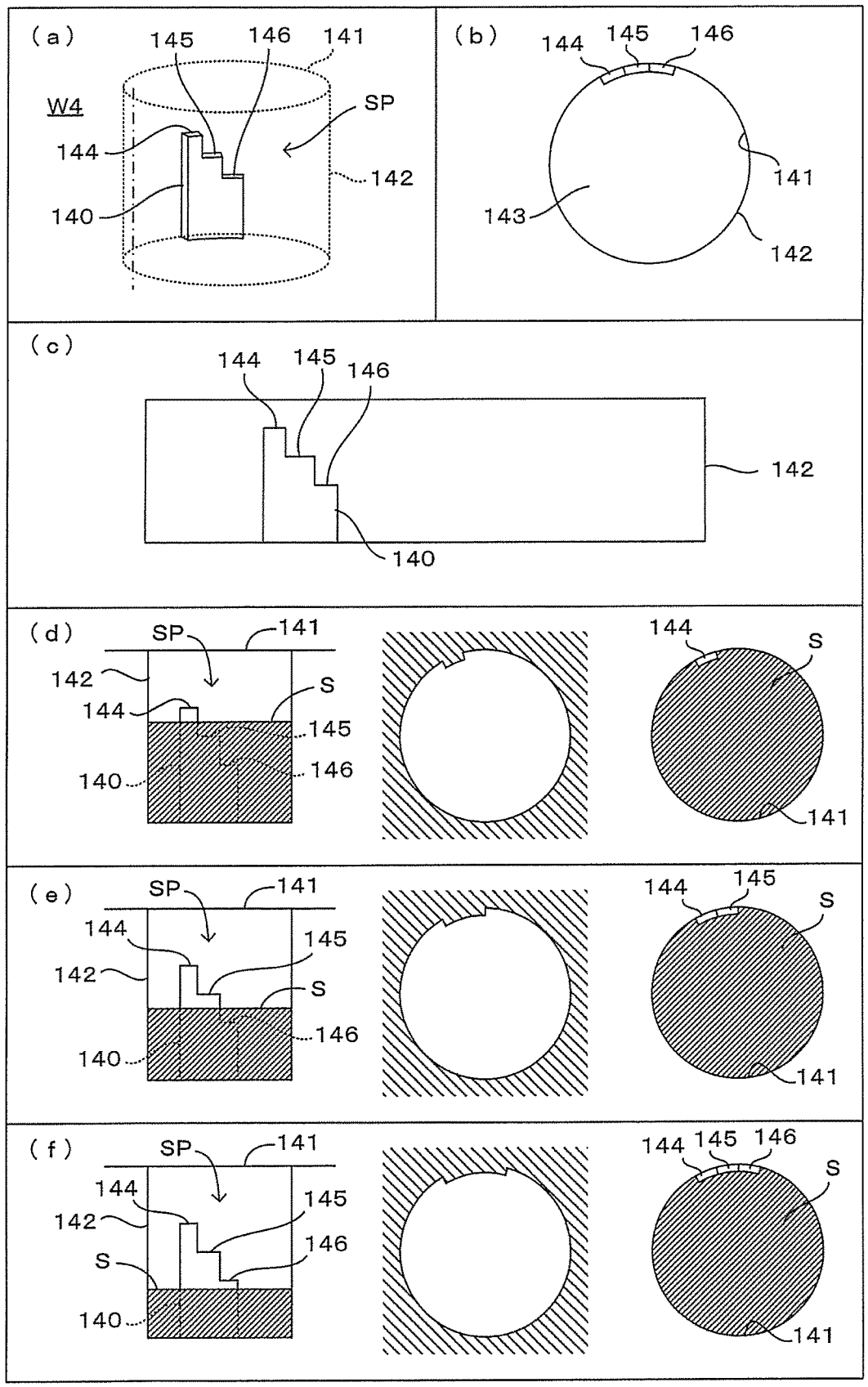
FIG. 5 is a drawing showing a fourth example of a well having an internal configuration according to the present invention.

FIG. 5 is a drawing showing a fourth example of a well having an internal configuration according to the present invention. A well W4 according to the fourth example includes a single rising portion 140 with a top changing in height at multiple stages provided to extend from a side wall 142 of the well W4 toward a central area in the well internal space SP, instead of the multiple rising portions according to the first example having different heights and arranged at intervals. Specifically, the rising portion 140 has an upper configuration of a staircase pattern including a planar section 144 at the height position, a planar section 145 at a lower position, and a planar section 146 at a still lower position in the internal space SP.

Thus, based on the same principle as that described above, as the fluid surface S drops, more planar sections of the rising portion 140 become exposed. In this way, a situation of exposure of each of the planar sections 144, 145, and 166 is changed when the fluid surface S is observed through an opening plane 141. Thus, like in the case of the first example, information about the height of the fluid surface S, specifically, about a fluid amount can be acquired based on a situation of exposure of each planar section observed from above.

Figure 6:
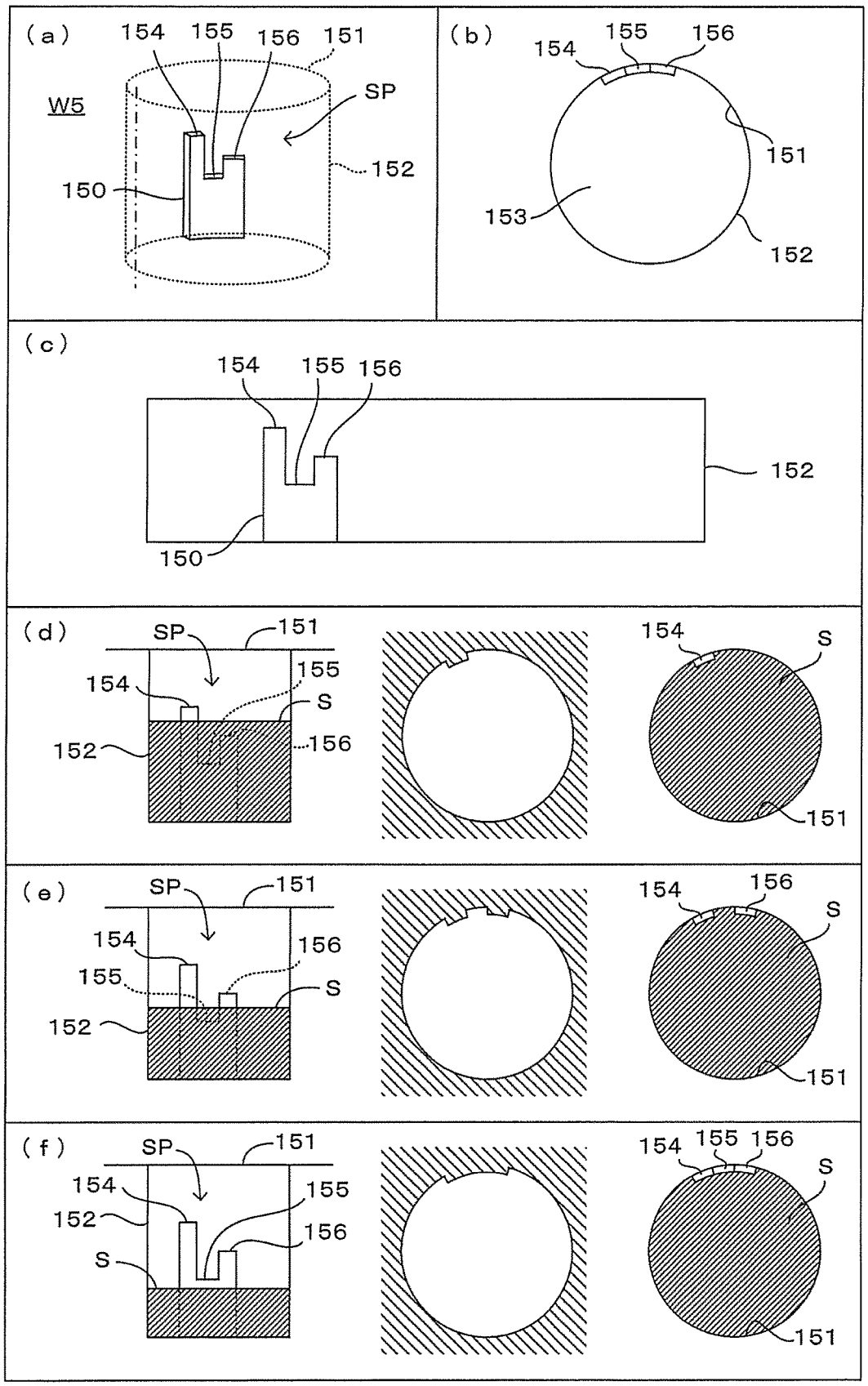
FIG. 6 is a drawing showing a fifth example of a well having an internal configuration according to the present invention.

FIG. 6 is a drawing showing a fifth example of a well having an internal configuration according to the present invention. According to the fourth example, the planar sections having heights changing sequentially are provided in a staircase pattern. Instead of this configuration, a well W5 according to the fifth example includes a rising portion 150 extending inwardly from a side wall 152. The rising portion 150 includes a highest planar section 154, a next highest planar section 156, and a lowest planar section 155 caught between the planar sections 154 and 156.

According to this example, as shown in the field (e), the planar sections 154 and 156 to become exposed from the fluid surface S when the height of the fluid surface S is at an intermediate position are recognized to be separated from each other through observation through an opening plane 151. Thus, the fifth example is an improvement on the fourth example in terms of the performance of distinguishing from the state shown in the field (d) and the state shown in the field (f).

As modifications of the fourth and fifth examples, the rising portions of each of the fourth and fifth examples may be configured to extend outwardly from the corresponding side wall. The following describes a well W6 according to a sixth example as a modification of the fourth example.

Figure 7:
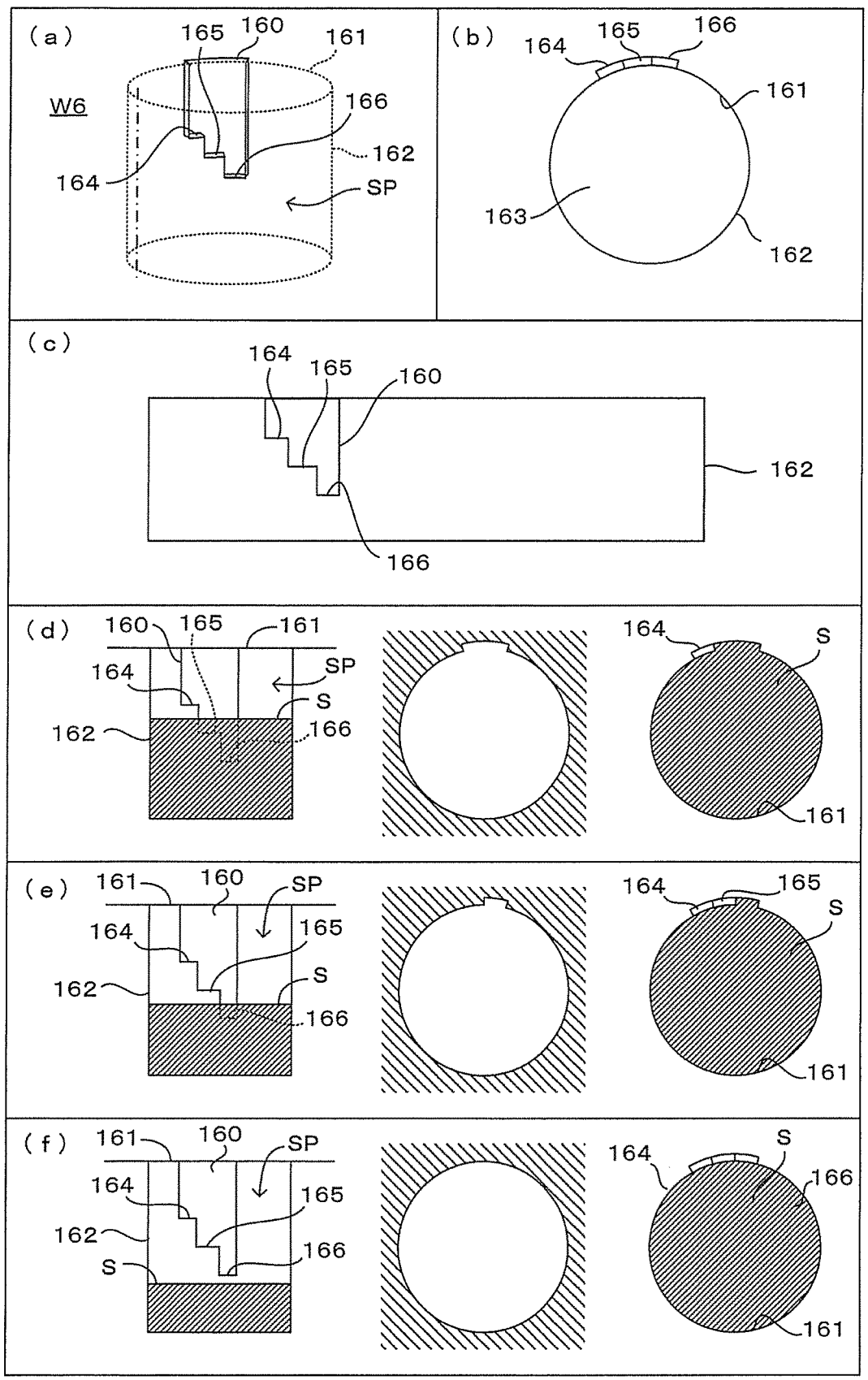
FIG. 7 is a drawing showing the sixth example of a well having an internal configuration according to the present invention.

FIG. 7 is a drawing showing the sixth example of a well having an internal configuration according to the present invention. The well W6 according to the sixth example includes a rising portion 160 with a bottom of a staircase pattern provided to extend outwardly from a side wall 162. Specifically, the rising portion 160 has a lower configuration of a staircase pattern including a planar section 164 at the height position, a planar section 165 at the next highest position, and a planar section 166 at the lowest position.

Also in this example, the outer peripheral shape of the cross section of the well W6 changes in response to the height of the fluid surface S, as shown in the fields (d) to (f). Together with this change, the shape of the fluid surface S and a situation of exposure of each of the planar sections 164, 165, and 166 change when the fluid surface S is viewed through an opening plane 161. Thus, like in the case of each of the foregoing examples, information about the height of the fluid surface S, specifically, about a fluid amount can be acquired based on a situation of exposure of each planar section observed from above.

Figure 8:
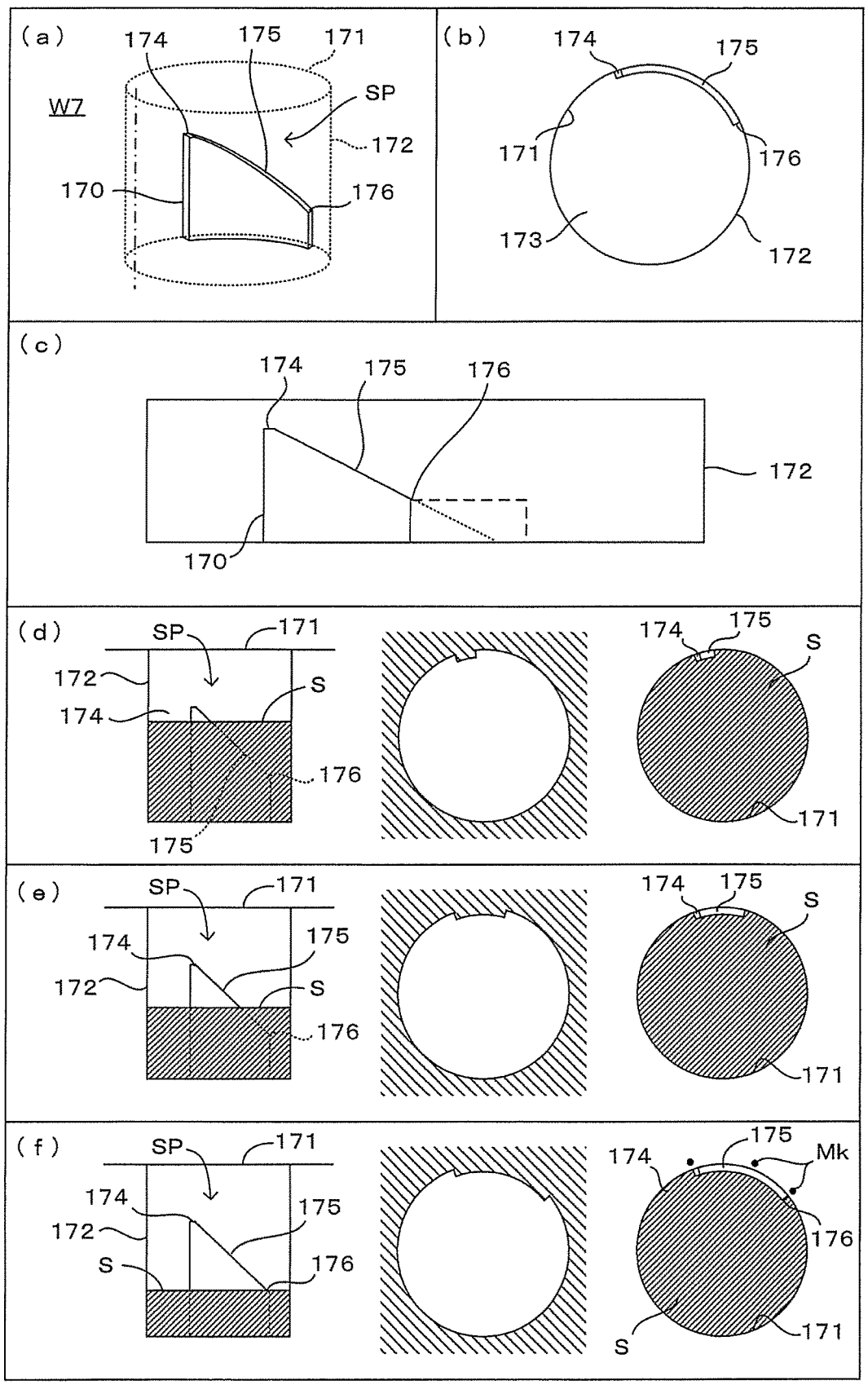
FIG. 8 is a drawing showing a seventh example of a well having an internal configuration according to the present invention.

FIG. 8 is a drawing showing a seventh example of a well having an internal configuration according to the present invention. A well W7 according to the seventh example includes a rising portion 170 with an upper surface at a height changing continuously provided to extend from a side wall 172 of the well W7 toward the center in the internal space SP, instead of the foregoing upper configuration of a staircase pattern according to the fourth example. More specifically, the rising portion 170 has a top functioning as a small-area planar section 174. A tilted surface section 175 continuous with the planar section 174 is a tilted surface extending along the side wall 172 and having a height continuously changing to a rear end 176 of the tilted surface section 175. Specifically, a normal line of the tilted surface section 175 contains a component pointing upwardly in the vertical direction and a component pointing in the horizontal direction. As shown by solid lines, a dotted line, and dashed lines in the field (c), the height of a section continuous with the rear end 176 may be changed freely. As long as a problem is not caused about manufacture, the planar section 174 may be omitted.

In the well W7 having the foregoing configuration, the length of exposure of the tilted surface section 175 from the fluid surface S increases in response to the height of the fluid surface S, as shown in the fields (d) to (f). This increases the area of a region corresponding to the rising portion 170 in a cross section. Thus, when the fluid surface S is viewed through an opening plane 171, the length of exposure of the tilted surface section 175 is increased in response to reduction in a fluid amount. Specifically, the height of the fluid surface S can be understood from conversion to the length of exposure of the tilted surface section 175.

To acquire an upper limit and a lower limit of a fluid amount and information indicating timing of adding a fluid more easily, appropriate markers Mk may be provided at the upper surface of a base material around the opening plane 171. The markers Mk can be formed by printing or engraving, for example. The amount of a held fluid can be shown quantitatively through observation through the upper surface based on the position of a tip area of the tilted surface section 175 extending longer with reduction in a fluid amount relative to the positions of the markers Mk.

Figure 9:
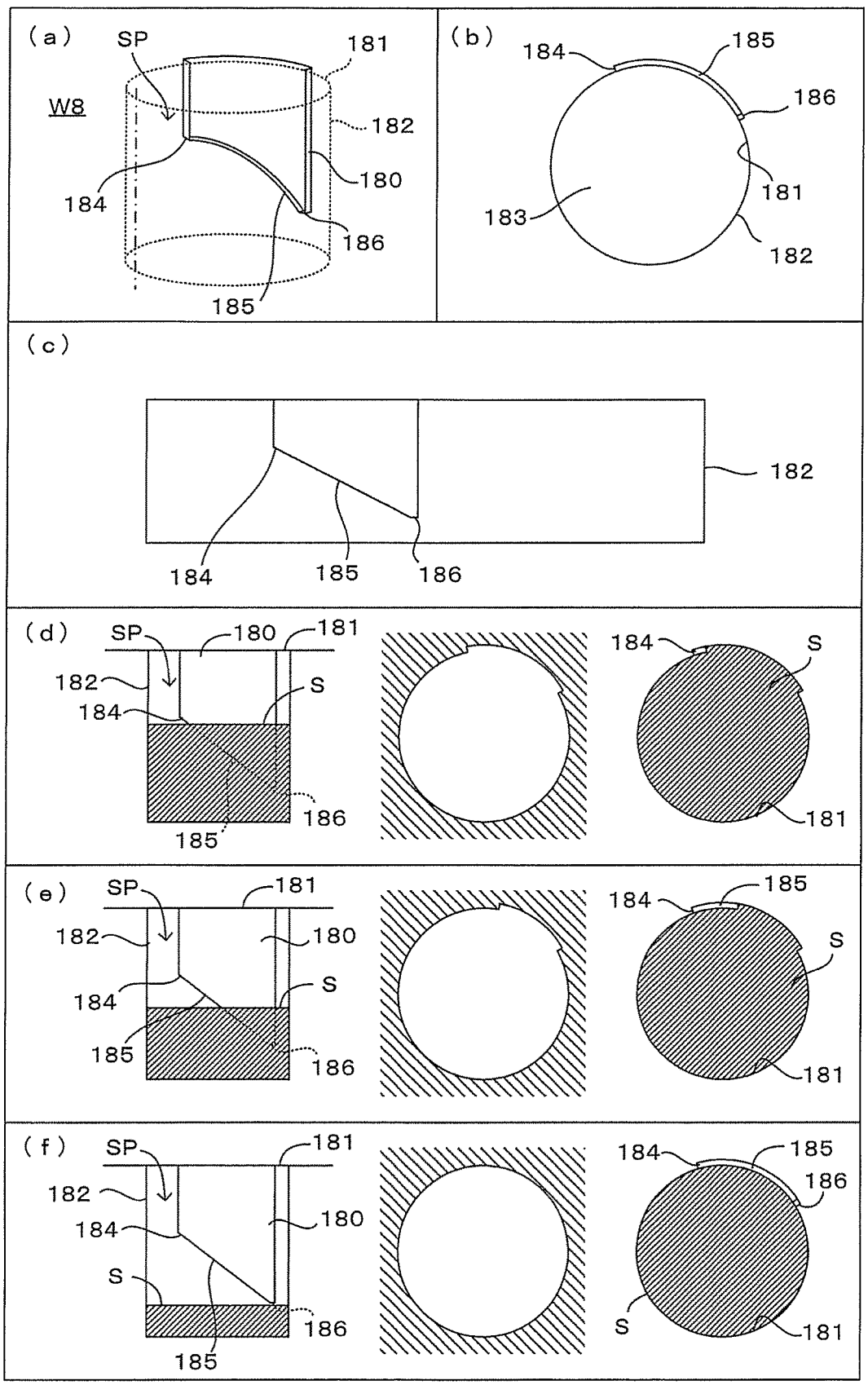
FIG. 9 is a drawing showing an eighth example of a well having an internal configuration according to the present invention.

FIG. 9 is a drawing showing an eighth example of a well having an internal configuration according to the present invention. A well W8 according to the eighth example includes a rising portion 180 with a bottom at a height changing continuously extending outwardly from a side wall 182, instead of the rising portion extending inwardly according to the foregoing seventh example. Like in the configuration of the seventh example, in this configuration, drop of the fluid surface S increases an exposed area of a tilted surface section 185 of the rising portion 180. This changes the shape of the fluid surface S and a situation of exposure of the rising portion 180 viewed through an opening plane 181.

More specifically, as shown in the field (d), when the fluid surface S is at a high position, only an upper end 184 and its vicinity of the tilted surface section 185 are exposed upwardly from the fluid surface S. As the fluid surface S drops, an exposed area of the tilted surface section 185 is increased. Observation from above shows that the rising portion 180 appearing at the outer periphery of the fluid surface S extends gradually longer. The position of a lower end 186 of the tilted surface section 185 can be learned from the shape of the fluid surface S. In this way, a degree of approximation of a fluid amount to a lower limit can be learned readily based on a distance from the tip of an exposed area of the tilted surface section 185 to the lower end 186 obtained through observation from above.

Figure 10A:
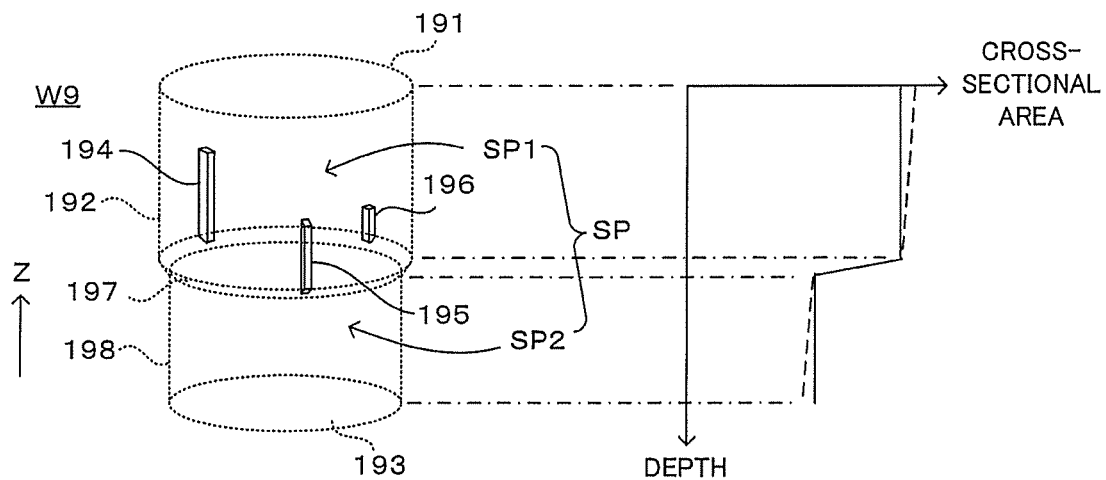
FIGS. 10A, 10B, and 10C are drawings showing a ninth example of a well having an internal configuration according to the present invention.
Figure 10B:
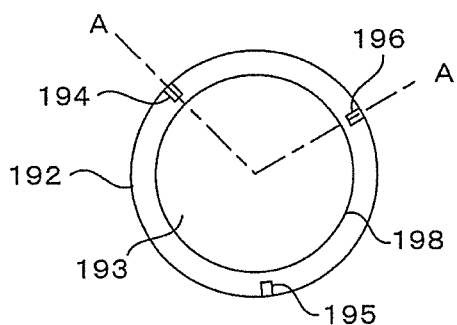
Figure 10C:
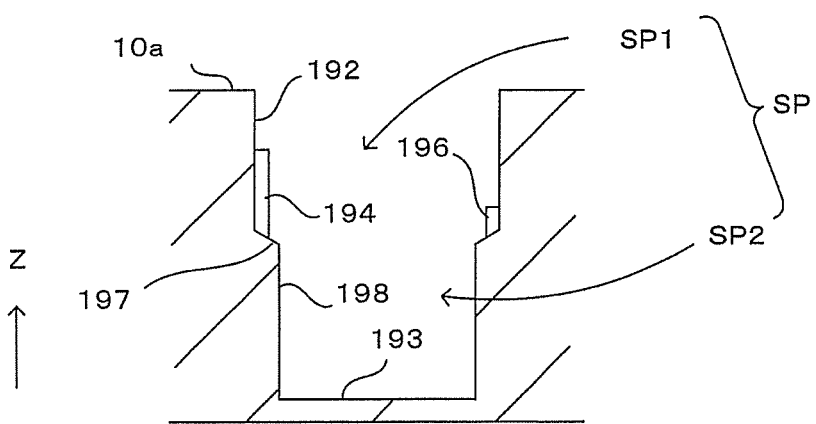

FIGS. 10A, 10B, and 10C are drawings showing a ninth example of a well having an internal configuration according to the present invention. More specifically, FIG. 10A is a transparent view showing the internal configuration of a well W9 according to the ninth example and a view showing change in the horizontal cross-sectional area of the well W9. FIG. 10B is a top view of the well W9. FIG. 10C is a sectional view taken along a line A-A of FIG. 10B.

The well W9 according to the ninth example has a different schematic shape taken at the vertical cross section of the internal space SP from the shape according to each of the foregoing examples. Specifically, the well W9 according to this example has a side wall having the following configuration extending from an opening plane 191 to a bottom surface 193. The side wall is configured in such a way that a first side wall 192 having a relatively large horizontal cross-sectional area and a second side wall 198 having a smaller horizontal cross-sectional area are connected through a diameter-reducing section 197 having a horizontal cross-sectional area rapidly reducing downwardly.

As shown in the right view of FIG. 10A, the horizontal cross-sectional area of the well internal space SP changes rapidly between an area ahead of the diameter-reducing section 197 and an area at the back of the diameter-reducing section 197. As indicated by dashed lines in this view, at least one of the side walls 192 and 198 may be formed into a tapered shape having a cross-sectional area reducing at a greater depth. In this case, a section where a rate of change in a cross-sectional area to change in a depth is considerably higher than change rates at different depths can be considered as the diameter-reducing section.

Specifically, the configuration of the internal space SP of the well W9 is such that first space SP1 defined by the side wall 192 and having a relatively large horizontal cross-sectional area and second space SP2 defined by the side wall 198 and having a smaller horizontal cross-sectional area are connected one above the other. The side wall of the well W9 has a level difference at the diameter-reducing section 197 corresponding to the connection between the first space SP1 and the second space SP2. In this regard, the diameter-reducing section 197 can also be called a "level difference section" forming a part of the side wall.

The side wall 192 above the diameter-reducing section 197 is provided with rising portions 194, 195, and 196 having comparable configurations and functions to the rising portions 114, 115, and 116 according to the foregoing first example (FIG. 2). In the right view of FIG. 10A, change in a cross-sectional area resulting from the rising portions is regarded as negligible. On the other hand, the side wall 198 below the diameter-reducing section 197 has a simple shape like a circular cylindrical surface. Alternatively, the side wall 198 may be tapered.

Figure 11:
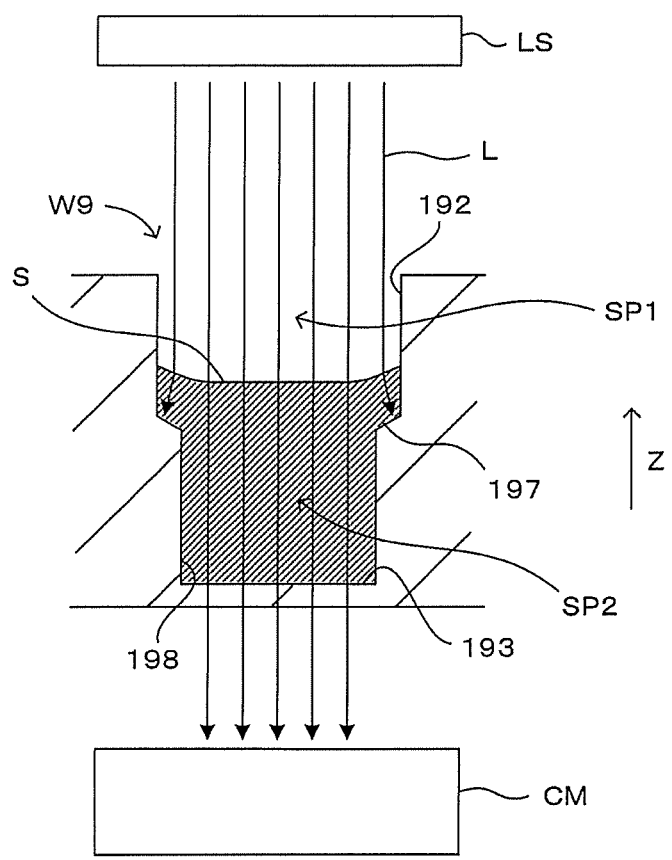
FIG. 11 is a drawing showing an example of image capture of a fluid held in a well having a level difference.

FIG. 11 is a drawing showing an example of image capture of a fluid held in a well having a level difference. In this example, image capture of a specimen in a fluid poured into the well W9 is explained. In this example, epi-illumination and transmission imaging are combined. However, this is not the limited imaging method. For example, a light source LS is arranged above the well W9 and illumination rays of light L emitted downwardly from the light source LS are caused to enter the well W9. An image of the interior of the well W9 can be captured by receiving rays of light traveling downwardly after passing through the well bottom surface 193 using image capture means CM.

The fluid surface S of the fluid poured into the well W9 forms bulging meniscuses at positions contacting the well side wall. Thus, some of the rays of light L entering the fluid surface S from above and impinging on regions near the side wall 192 are bent externally by the lens effect occurring at the fluid surface. This disables sufficient rays of light to enter a peripheral part of a bottom surface in a conventional and ordinary well in which the internal space SP has a horizontal cross-sectional area constant in the depth direction (alternatively, the internal space SP has continuous and monotonous tiny changes), for example. This causes a problem that the peripheral part of the bottom surface is also darkened in a resultant image.

By contrast, in the well W9 having the foregoing configuration, the rays of light bent by the meniscuses are blocked by the diameter-reducing section 197. This makes it possible to obtain substantially uniform illumination conditions at the bottom surface 193. As a result, sufficient brightness can be ensured in a captured image including the peripheral part.

To achieve such an advantage, a fluid should be poured to reach a position above the diameter-reducing section 197. In this regard, the well W9 described in this example includes the rising portions provided above the diameter-reducing section 197 to allow learning of the height of the fluid surface S through observation from above, as described above. Applying visualization of a fluid surface height realized by the rising portions to a well having such a configuration makes it possible to easily determine whether a fluid of an appropriate amount is held through observation from above. This allows addition of the fluid, if necessary. In this example, the rising portions described as the first example are combined with the well having a level difference. Alternatively, this well can be combined with a configuration according to any of the other examples.

By contrast to a conventional well having a relatively simple cross-sectional shape such as a circle or a rectangle, each of the wells W (W1 to W9) having the foregoing configurations includes a rising portion extending externally or internally partially provided at the contour of a cross section. Thus, a cross-sectional shape changes in response to a fluid amount to allow learning of a fluid amount through visual check from above. If a fluid amount is determined to be insufficient, addition of a fluid is required. Further, to remove a metabolite resulting from activation of a cell or the like, a fluid may be exchanged regularly. The following describes how the configuration of each of the foregoing wells acts for such operation.

Regarding pouring of a culture fluid into a well or exchange of the culture fluid in the well, a required amount of the fluid or required work may differ between wells. This requires operator's work by hand while requiring check of the state of the fluid in each well by the operator. More specifically, the required work is such that a tool for fluid pouring such as a pipette with a thin tip is inserted into a well through the top of the well and the fluid of a required amount is poured into the well. In this case, it is difficult to determine the position of the tip of the tool promptly and correctly by hand relative to the well. Hence, even a skilled person still takes time in doing the work. Additionally, the fluid may leak out of the well or the amount of the poured fluid may be incorrect.

In this regard, the well having each of the foregoing configurations includes a rising portion provided at the side wall for learning of a fluid amount. This rising portion is also functional as a reference for the operator to determine the position of the tool. Specifically, the operator holding the tool is allowed to easily fix the position of the tip of the tool relative to the well by making the tip of the tool abut on the rising portion. This allows the work of pouring the fluid to be done promptly and correctly. Regarding exchange of the culture fluid, by making the tip of a pipette for sucking the culture fluid from a well abut on any rising portion and sucking the old culture fluid in the well, the culture fluid can be removed promptly to an intended fluid surface height while the old culture fluid of a constant amount remains in the well. By doing so, even an unexperienced person can still exchange the culture fluid of a correct amount.

To assist in such work more effectively, the rising portion may be configured as follows. Regarding several modifications described below, wells are illustrated only partially in the drawings and the wells are described only partially. However, ideas of the modifications are also applicable to parts not illustrated in the drawings and not described below and such parts can be modified in the same way.

FIGS. 12A through 12C and FIGS. 13A through 13D are drawings each showing a modification of the shape of the rising portion. In the well W1 having the configuration where the rising portions extend internally from the well side wall as shown in FIG. 2, for example, a fluid poured from the top of the well W1 may adhere to the top surface of the rising portion 114, 115, or 116 to mask this rising portion. In this regard, in a well W11 according to a modification shown in FIG. 12A, the rising portion 114a has an upper surface 114b formed as a tilted surface having a downward inclination in a direction from a side wall 112a toward a well center area. In this configuration, a fluid flows down without staying at the upper surface 114b of the rising portion 114a. This prevents the fluid from remaining at the upper surface 114b. An angle θ formed between the upper surface 114b and the vertical direction is preferably from 30 to 60 degrees and can be set at 45 degrees, for example. This angle also applies to the angle θ according to each of the following modifications.

Figure 12A:
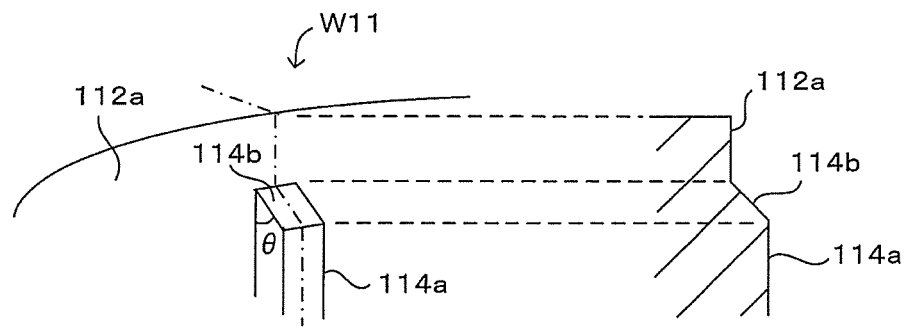
FIGS. 12A through 12C and FIGS. 13A through 13D are drawings each showing a modification of the shape of the rising portion.
Figure 12B:
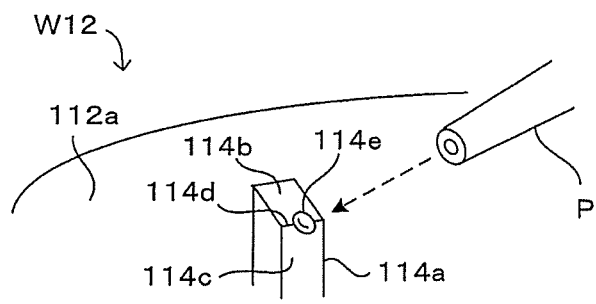

In a well W12 according to a modification shown in FIG. 12B, the modification in FIG. 12A is modified further. Specifically, an outwardly-pointing recess 114e is provided so as to cover a part of an edge line portion 114d where the upper surface 114b and a lateral surface 114c of the rising portion 114a are connected. The shape of the recess 114e is not limited to the shape illustrated in FIG. 12B but may be determined freely.

Figure 12C:
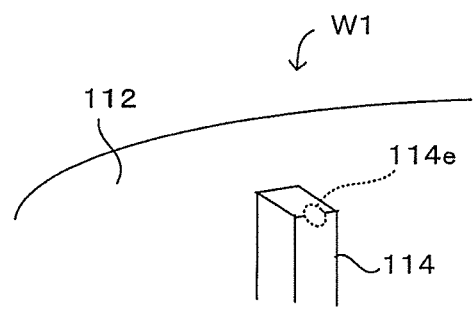

In this configuration, if an operator makes a tip P of a tubular pipette held by the operator abut on the recess 114e, movement of the pipette tip P in the horizontal direction is restricted. This makes it possible to determine the position of the pipette tip P easily and correctly. This configuration is also applicable in the same way to the rising portion 114 of the well W1 having a horizontal upper surface as shown in FIG. 12C.

Figure 13A:
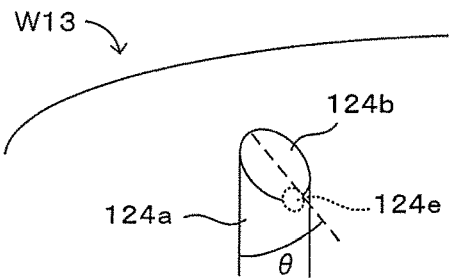
Figure 13B:
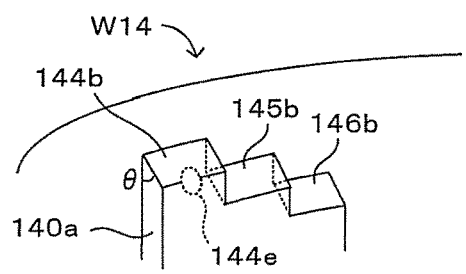
Figure 13C:
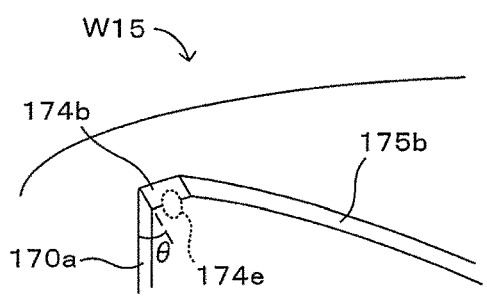

FIGS. 13A, 13B, and 13C show a modification of the well W2 shown in FIG. 3, a modification of the well W4 shown in FIG. 5, and a modification of the well W7 shown in FIG. 8 respectively. In a well W13 according to the modification shown in FIG. 13A, a rising portion 124a of a columnar shape extending upwardly from a well bottom surface has an upper surface 124b formed as a tilted surface having a downward inclination in a direction from a side wall toward a well center area. In this case, a recess 124e for abutting contact by a pipette may also be provided, as shown by a dotted line.

In a well W14 according to the modification shown in FIG. 13B, a rising portion 140a formed into a staircase pattern has upper surfaces 144b, 145b, and 146b, and each of these upper surfaces is formed as a tilted surface having a downward inclination in a direction from a side wall toward a well center area. In this case, a recess 144e for abutting contact by a pipette may also be provided. In the illustration of this example, the recess 144e is given only to the upper surface 144b forming the staircase pattern. Alternatively, recesses may also be given to the other upper surfaces 145b and 146b.

In a well W15 according to the modification shown in FIG. 13C, a rising portion 170a has a planar section 174b at the upper end formed as a tilted surface having a downward inclination in a direction from a side wall toward a well center area. A tilted surface section 175b has a peripheral inclination, so that it can be determined freely whether to provide the tilted surface section 175b with an inclination in a direction from the side wall toward the wall center area, specifically, in a radial direction. In this case, a recess 174e for abutting contact by a pipette may also be provided.

Figure 13D:
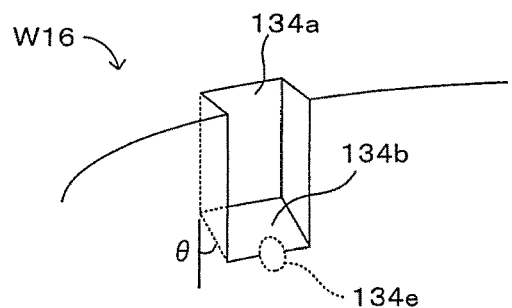

The modification shown in FIG. 13D is a modification of the well W3 shown in FIG. 4. In the well W3, the rising portion 134 itself extending externally from the well opening plane 131 is functional as a positional reference for abutting contact by a pipette. Then, in a well W16 according to the corresponding modification, a rising portion 134a has a lower surface 134b formed as a tilted surface for preventing a poured fluid from adhering to the lower surface 134b. In this case, a recess 134e for abutting contact by a pipette may also be provided.

Based on the same idea as that described above, modifications of the wells not described herein may be devised as follows. Regarding a well including a rising portion with an upper surface, the upper surface is formed as a tilted surface. Regarding a well including a rising portion with a lower surface, the lower surface is formed as a tilted surface. By doing so, a poured fluid is allowed to flow down without being accumulated. Additionally, providing a recess on an as-needed basis can enhance performance of work of pouring the fluid and enhance working accuracy.

In particular, exchange of a culture fluid causes risk of damage on a cell or the like being cultured due to contact by the tip of a tool inserted into a well. In this regard, the foregoing configurations facilitate positioning of the tool tip to avoid such a problem.

As described above, according to the foregoing embodiment, the well plate 10 functions as the "specimen container" of the present invention. Above all, the base material 11 functions as the "body" of the present application. Regarding the configuration of each of the foregoing examples including multiple rising portions, these rising portions function together as the "rising part" of the present invention. Regarding the configuration with a single rising portion, this rising portion corresponds to the "rising part" of the present invention.

In each of the examples shown in FIGS. 2 to 9, assuming that the depth of the fluid surface S from an opening plane shown in the field (d) in each of these figures is the "first depth," the cross section of the internal space SP at this stage corresponds to the "first cross section" of the present invention. The depth of the fluid surface S from the opening plane shown in each of the field (e) and the field (f) corresponds to the "second depth" relative to the first depth. Further, the cross section of the internal space SP at this stage corresponds to the "second cross section" of the present invention. Meanwhile, assuming that the depth of the fluid surface S from the opening plane shown in the field (e) in each of these figures is the "first depth," the depth of the fluid surface S from the opening plane shown in the field (f) corresponds to the "second depth" relative to the first depth.

Note that the invention is not limited to the above embodiment and various changes other than those described above can be made without departing from the gist of the invention. For example, the well according to each of the foregoing examples has a schematic circular horizontal cross section. However, the applicability of the present invention is not limited to this shape but the present invention is further applicable to a well having a rectangular cross section, for example.

In some of the foregoing examples, the rising portion has a height differing at three stages. However, the height may differ at any number of stages of two or more.

Further, in each of the foregoing examples, the opening of the well and a horizontal plane agree with each other. Alternatively, the opening is not always required to be horizontal. In this case, the shape of the opening projected on an appropriate horizontal plane may be defined as the shape of an opening plane. The configuration of the well may be realized in such a manner that each cross section taken at a deeper position is contained in the opening plane in a plan view.

The foregoing well plate 10 includes the multiple wells W each capable of holding a fluid in the well W. However, the "specimen container" of the present invention is not limited to such a configuration. For example, the present invention is also applicable to a specimen container known by a name such as "dish" or "Petri dish" including only one storage space for storing a fluid.

As described above by giving the specific embodiment, in an applicable configuration, the specimen container according to the present invention may include a rising part extending from the side wall of the well toward a center area in internal space of the well. The rising part includes a portion appearing in the first cross section and absent in the second cross section, and a portion appearing both in the first cross section and the second cross section, for example. In another application configuration, a part of the side wall of the well may form a rising part extending in an external direction from the internal space. The rising part includes a portion appearing in the first cross section and absent in the second cross section, and a portion appearing both in the first cross section and the second cross section, for example.

In these configurations, the number of the rising parts appearing at a fluid surface or the shape of the rising part changes in response to a fluid amount. Specifically, a fluid amount in the well can be shown visually based on the number of the rising parts appearing at the fluid surface or the shape of the rising part through viewing from above.

In these cases, the rising part may be configured to have multiple top faces at different heights in the vertical direction each bordering the internal space. More specifically, the rising part may be configured in such a manner that the rising part includes multiple columnar portions extending in the vertical direction and are arranged along the side wall of the well, and each of the columnar portions has the top face, for example. In this configuration, a columnar portion having a top face above the fluid surface is recognized as being exposed from the fluid surface when viewed from above. Meanwhile, a columnar portion having a top face below the fluid surface is hidden under the fluid. Based on this difference in the vision, a fluid amount can be determined.

The rising part may have any of the following configurations:

(1) A configuration where the rising part has a top face, a normal of the top face contains a component pointing upwardly in the vertical direction, and a height of the top face changes continuously in the horizontal direction.

(2) A configuration where the rising part has multiple bottom faces at different heights in the vertical direction each bordering the internal space.

(3) A configuration where the rising part includes multiple grooves extending in the vertical direction and are arranged along the side wall, and each of the groove portions has the bottom face.

(4) A configuration where the rising part has a bottom face, a normal of the bottom face contains a component pointing upwardly in the vertical direction, and a height of the bottom face changes continuously in the horizontal direction.

In any of these configurations, a difference in a fluid surface height resulting from a difference in a fluid amount changes the shape of the fluid surface in response to a fluid amount when the fluid surface is viewed from above. This makes it possible to easily recognize a fluid amount visually based on the shape of the fluid surface.

Each of the foregoing configurations may further be configured in such a manner that a horizontal cross section of the internal space taken at one depth position in the vertical direction covers a horizontal cross section of the internal space taken at any position deeper than the one depth position in a plan view, for example. In this configuration, the shape of the fluid surface at the stage of a small fluid amount has a cutout formed at a part of the shape of the fluid surface at the stage of a larger fluid amount. Additionally, there is no structure above the fluid surface to block the shape of the fluid surface. This makes it possible to learn the shape of the fluid surface accurately through observation from above.

In another applicable configuration, the side wall may form a level difference section at a position of a predetermined height in the vertical direction, and the horizontal cross-sectional area of the internal space is smaller at a position below the predetermined height than at a position above the predetermined height. Further, the second cross section is a horizontal cross section above the level difference section, for example. Knowledge of the present inventors shows that the well with this level difference section is usable in suppressing a phenomenon that the edge of a well bottom surface is darkened due to a meniscus occurring at the fluid surface. This effect is achieved by the position of the fluid surface higher than the level difference section. Thus, if drop of the fluid surface to a position below the level difference section can be detected before this drop occurs, the foregoing effect can be achieved more reliably.

In another applicable configuration, the second cross section corresponds to a lower limit of a fluid surface height of the fluid stored in the internal space, for example. In this configuration, a fluid amount can be determined to exceed or fall below the lower limit based on change in the shape of the fluid surface. This makes it possible to take action such as addition of the fluid on an as-needed basis, for example.

In another applicable configuration, if the rising part has a top face, the top face is a tilted downwardly from the side wall of the well toward the center in the internal space. If the rising part has a bottom face, the bottom face is the tilted surface, for example. As another example, a connecting part between a top face and the side surface of the well may have an outwardly-pointing recess. These configurations can enhance performance of work of pouring the fluid into the well with a tool for fluid pouring by an operator and working accuracy.

The present invention is applicable to all types of specimen containers for holding substances to be cultured such as cells and a fluid together. The present invention is applicable particularly preferably for the purpose of using a specimen prepared by the culture for image capture. Such specimen containers are preferably applicable to fields such as medical, biochemical, and drug development fields.

Although the invention has been described with reference to specific embodiments, this description is not meant to be construed in a limiting sense. Various modifications of the disclosed embodiment, as well as other embodiments of the present invention, will become apparent to persons skilled in the art upon reference to the description of the invention. It is therefore contemplated that the appended claims will cover any such modifications or embodiments as fall within the true scope of the invention.

What is claimed is:

1. A specimen container, comprising a body to which a well having an opening at an upper end and capable of storing a fluid in internal space is disposed, wherein:
    a part of an inner side wall facing the internal space of the well forms a rising part which has a groove-like shape projecting in an external direction from the internal space and extends vertically from a circumference of the opening to at least a first depth, thereby partially extending the internal space outwardly,
    in a plan view, a first cross section of the well is contained in an opening plane of the well and a second cross section of the well is contained in the first cross section,
    the rising part includes: a portion appearing in the first cross section and absent in the second cross section; and a portion appearing both in the first cross section and the second cross section, and
    the opening plane, the first cross section and the second cross section is defined in a horizontal posture of the body as follows:
        the opening plane is a projected plane of the opening of the well on a horizontal plane;
        the first cross section is a horizontal cross section of the internal space of the well taken at a position corresponding to the first depth defined vertically downwardly from the opening; and
        the second cross section is a horizontal cross section of the internal space of the well taken at a position corresponding to a second depth greater than the first depth.

2. The specimen container according to claim 1, wherein the rising part includes a plurality of bottom faces at different heights in a vertical direction and each of the bottom faces borders the internal space.

3. The specimen container according to claim 2, wherein the rising part includes multiple grooves extending in the vertical direction and are arranged along the inner side wall, and each of the grooves has the bottom face.

4. The specimen container according to claim 2, wherein the bottom face is tilted downwardly from the inner side wall toward a center in the internal space.

5. The specimen container according to claim 2, wherein an outwardly-pointing recess is disposed to a connecting part between the bottom face and a side surface of the well, the side surface being different from a surface of the rising part.

6. The specimen container according to claim 1, wherein
    the rising part is a single groove which is disposed to the inner side wall along a circumference of the well and includes a bottom face, and
    a normal of the bottom face contains a component pointing upwardly in a vertical direction and a height of the bottom face changes continuously in a circumferential direction of the well.

7. The specimen container according to claim 1, wherein a horizontal cross section of the internal space taken at one depth position in a vertical direction covers a horizontal cross section of the internal space taken at any position deeper than the one depth position in a plan view.

8. The specimen container according to claim 1, wherein a level difference section is formed to the inner side wall of the well at a position of a predetermined height in a vertical direction and a horizontal cross-sectional area of the internal space is smaller at a position below the predetermined height than at a position above the predetermined height.

9. The specimen container according to claim 1, wherein the second cross section corresponds to a lower limit of a fluid surface height of the fluid stored in the internal space.

10. A specimen container, comprising a body to which a well having an opening at an upper end and capable of storing a fluid in internal space is disposed, wherein:
    a part of an inner side wall facing the internal space of the well forms a rising part that projects toward the internal space and extends upwardly from a bottom of the well along a circumference of the well, and
    a top face of one rising part changes in height in a circumferential direction of the inner side wall and includes:
        one portion appearing in a second cross section and absent in a first cross section; and
        another portion disposed to a different position from the one portion in the circumferential direction and appearing both in the first cross section and the second cross section,
    the first cross section and the second cross section is defined in a horizontal posture of the body as follows:
    the first cross section is a horizontal cross section of the internal space taken at a position corresponding to a first depth defined vertically downwardly from the opening; and
    the second cross section is a horizontal cross section of the internal space taken at a position corresponding to a second depth greater than the first depth.

11. The specimen container according to claim 10, wherein the top face of the rising part includes a plurality of surfaces at different heights in a vertical direction and each of the surfaces borders the internal space.

12. The specimen container according to claim 10, wherein
    a normal of the top face contains a component pointing upwardly in a vertical direction and a height of the top face changes continuously in a circumferential direction of the well.

13. The specimen container according to claim 10, wherein the top face is tilted downwardly from the inner side wall toward a center in the internal space.

14. The specimen container according to claim 10, wherein a horizontal cross section of the internal space taken at one depth position in a vertical direction covers a horizontal cross section of the internal space taken at any position deeper than the one depth position in a plan view.

15. The specimen container according to claim 10, wherein a level difference section is formed to the inner side wall of the well at a position of a predetermined height in a vertical direction and a horizontal cross-sectional area of the internal space is smaller at a position below the predetermined height than at a position above the predetermined height.

16. The specimen container according to claim 10, wherein the second cross section corresponds to a lower limit of a fluid surface height of the fluid stored in the internal space.

* * * * *